(12) United States Patent
Morishima et al.

(10) Patent No.: US 6,417,336 B1
(45) Date of Patent: Jul. 9, 2002

(54) ANTIBODY AGAINST CLEAVAGE PRODUCT OR VIMENTIN

(75) Inventors: Nobuhiro Morishima; Keiko Nakanishi; Takehiko Shibata, all of Saitama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/610,401

(22) Filed: Jul. 5, 2000

(30) Foreign Application Priority Data

Jul. 7, 1999 (JP) .......................................... 11-193235

(51) Int. Cl.$^7$ ................................................ C12P 21/08
(52) U.S. Cl. ................................ 530/387.9; 530/389.1; 435/7.1
(58) Field of Search ........................ 435/7.1; 530/387.1, 530/388.1, 389.1, 387.9; 436/500

(56) References Cited

PUBLICATIONS

Prasad, SC, et al, 1998, Apoptosis–associated proteolysis of vimentin in human prostate epithelial tumor cells, Biochemical and Biophysical Research Communications, vol. 249, pp. 332–338.*

Morishima, N, 1999, Changes in nuclear morphology during apoptosis correlate with vimentin cleavage by different caspases located either upstream or downstream of Bcl–2 action, Genes to Cells, vol. 4, pp. 401–414.*

Niccoli, P, et al, 1996, Interest in epitopic dissection in immunoanalysis of proteins and peptides: review of theoretical and practical aspects, European Journal of Clinical Chemistry and Clinical Biochemistry, vol. 34, pp. 741–748 (abstract only).*

Prasad S., et al., "Intermediate filament proteins during carcinogenesis and apoptosis (Review)." International Journal of Oncology, vol. 14, No. 3, Mar. 1999, pp. 563–570, XP000952788.

Masaki, I., Anti–(CDC) 2 Kinase—Phosphorylated Vimentin Monoclonal Antibody Patent Abstracts of Japan, JP 07 258296 A, Oct. 9, 1995.

Schmidt, M., et al. A monoclonal antibody directed against the head region of vimentin, Biochemical and Biophysical Research Communications, vol. 146, No. 3, 1987, pp. 1366–1374, XP002150823.

Hashimoto, M., et al., Rapid fragmentation of vimentin in human skin fibroblasts exposed to taxoxifen: A possible involvement of capase–3, Biochemical and Biophysical Research Communications, vol. 247, No. 2 Jun. 18, 1998, pp. 401–406, XP002150825.

* cited by examiner

*Primary Examiner*—Donna C. Wortman
*Assistant Examiner*—Stephen L. Rawlings
(74) *Attorney, Agent, or Firm*—Roberts & Mercanti LLP (57) ABSTRACT

The present invention provides the antibody that react with the cleavage product of vimentin, but not with intact vimentin.

9 Claims, 4 Drawing Sheets

Cleavage of vimentin in Jurkat cells undergoing apoptosis

Figure 3

Treatment with
anti-Fas antibody (hrs)

Anti-V1 antibody

Treatment with
anti-Fas antibody (hrs)

Anti-V2 antibody

Figure 4

Staining with anti-V2 antibody

DAPI staining

Small arrows indicate nuclei of apoptotic cells.
Large arrows indicate nuclei of normal cells.

ANTIBODY AGAINST CLEAVAGE PRODUCT OR VIMENTIN

FIELD OF THE INVENTION

The present invention relates to an antibody against the cleavage product of vimentin; a method for detecting apoptosis using this antibody; and a use for this antibody.

BACKGROUND OF THE INVENTION

Apoptosis is cell death in multicellular organisms. Surplus cells generated during developmental processes, cells no longer needed in an adult, cells damaged by radiation or chemical substances, or dangerous cells such as tumor cells are led to cell death by apoptosis, thus removed from a body.

Caspases are proteolytic enzymes (protease) that play a key role during apoptosis. Research on apoptosis has rapidly expanded since the 1990s. One of the key factors to have promoted the research is the identification of a caspase family of proteases that involves execution of apoptosis (Thomberry, N. & Lazebnik, Y. (1998) Science, 281, 1312–1316). At least 10 or more members of the caspase family are identified in mammals. Caspases are also shown to be present as an inactive precursor in normal cells. When apoptosis is initiated for a cell to die, an initiator caspase in the caspase family activates itself by limited proteolysis (processing). The activated initiator caspase activates another caspase by partially cleaving it, the cleaved caspase activates another caspase, and the process continues one after another. This amplification cascade mechanism is thought to achieve the whole activation. All caspases cleave the C-terminal side of a specific aspartic acid residue in protein, but the cleavage efficiency of each member of the caspase family varies depending on amino acid sequences near the cleavage site.

Apoptosis triggered by the stimulation of the anti-Fas antibody is the best analyzed apoptosis and thought to play a central role among adults (Nagata, S. (1997) Cell 88, 355–365). Caspase-8, involving execution of apoptosis is first activated among the caspase family in cells after stimulation with the anti-Fas antibody, and functions as an initiator (Boldin, M. P., Goncharov, T. M., Goltsev, Y. V. & Wallach, D. (1996) Cell 85, 803–815; Muzio, M., Chinnaiyan, A. M., Kishkel, F. C., O'Rourke, K., Shevchenko, A., Ni, J., Scaffidi, C., Bretz, J. D., Zhang, M., Gentz, R., Mann, M., Krammer, P. H., Peter, M. E. & Dixit, V. M. (1996) Cell, 85, 817–827).

Several methods for detecting activation of a caspase have been employed, such as 1) detecting processing of a caspase or activation using an antibody recognizing a caspase; or 2) measuring protease activity using a substrate analog. Any of these methods, however, have a drawback in that the ability to distinguish between members of caspase family is limited. In the method of 1), production of a specific antibody capable of recognizing both an inactive precursor and an active type is often difficult.

SUMMARY OF THE INVENTION

It is the objective of the present invention to provide an antibody against the cleavage product of vimentin that is a main component of an intracellular skeletal protein; a method for detecting apoptosis using said antibody; and the use of said antibody.

As a result of intensive and extensive research toward the above-mentioned objective, the inventors have finally found that vimentin in an apoptotic cell is specifically cleaved by caspase-8, and they have succeeded in producing an antibody capable of detecting the specific cleavage of vimentin.

That is, the present invention relates to an antibody that reacts with the cleavage product of vimentin but does not react with intact vimentin. The cleavage product of said vimentin is the one cleaved by action of caspase (e.g., caspase-8). The abovementioned antibody can be either a polyclonal antibody or a monoclonal antibody.

Further, the present invention relates to a method for detecting caspase activity or a method for detecting apoptosis, comprising allowing the above antibody to react with cleavage product of vimentin and detecting the resulting reaction product.

Furthermore, the present invention relates to a reagent for detecting apoptosis containing the above antibody.

The present invention will now be described in detail. This specification includes part or all of the contents as disclosed in the specification and/or drawings of Japanese Patent Application No. 11-193235, which is a priority document of the present invention.

DETAILED DESCRIPTION OF THE INVENTION

The present invention relates to an antibody specifically recognizing cleavage product of vimentin but not reacting with the whole vimentin (intact vimentin), a substrate of a caspase (e.g., caspase-8) activated at the initial stage of apoptosis. To detect the activity of caspases, the present inventors have produced an antibody reacting with a cleavage site of a substrate cleaved by a caspase by focusing on changes in the substrate (vimentin) not on the caspase itself. Therefore, activation of a caspase can now be detected with high sensitivity regardless of sample scale, such as tissue and cell.

Among amino acid sequences of vimentin protein, the present inventors have identified an aspartic acid residue at a specific site which is cleaved by caspase-8. Oligopeptides having a sequence on N-terminal side or C-terminal side of the aspartic acid residue are chemically synthesized and used for immunizing a rabbit. After several times of immunization, anti-serum is obtained. Then an antibody that binds strongly to the oligopeptide used for immunization in anti-serum is purified. The purified antibody does not bind to an intact vimentin protein, but specifically binds to a product cleaved by caspase-8. By using this antibody in the Western blot analysis and immunostaining of cells and tissues, the detection of activation of caspse-8 becomes possible through cleavage of vimentin either in vitro, in tissue sample or in cell sample.

The term "antibody" in the present invention represents the whole antibody molecule or its fragments (e.g., Fab or F(ab')$_2$ fragment), which can bind to the cleavage product of vimentin as an antigen. This antibody of this invention may be a polyclonal or monoclonal antibody. Antibodies of the present invention can be produced by various methods. Such production methods of antibodies are known in the art. (For example, see Harlow E. & Lane D., Antibody, Cold Spring Harbor Laboratory Press (1988))

1. Preparation of Antibodies Reacting with Cleavage Products of Vimentin (1) Preparation of Antigens Vimentin on which caspases act is an intermediate filament protein, characteristics in mesenchymal cells, such as fibroblasts and leukocytes.

Figure 1:
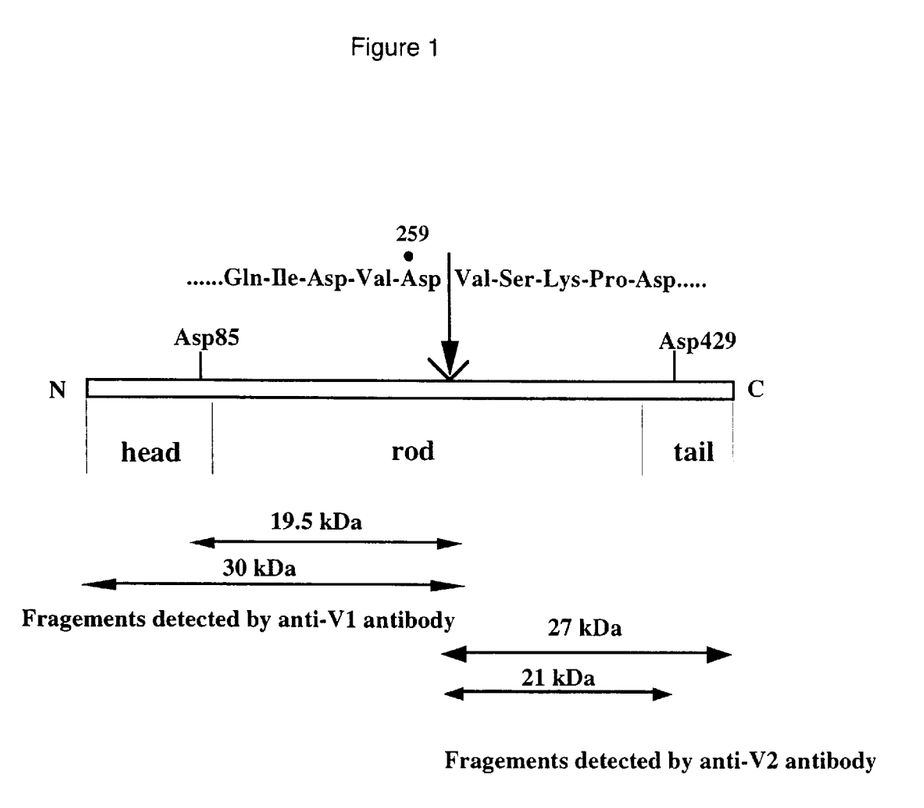
FIG. 1 shows a schematic diagram of the cleavage site by caspase in vimentin.

FIG. 1 is a scheme showing a site of an intermediate filament protein, vimentin, to be cleaved by a caspase when apoptosis is initiated by treatment with anti-Fas antibody. Caspases used in the present invention include caspase-3, caspase-6 or caspase-8, preferably, caspase-8. For example, caspase-8 recognizes and cleaves C terminal side of Asp-259 of an amino acid sequence of vimentin in a human or mouse (SEQ ID NO: 3 for a human, SEQ ID NO:4 for a mouse). Caspase-3 recognizes and cleaves C-terminal side of Asp-85; caspase-6 recognizes and cleaves C terminal side of Asp-429. According to the present invention, the two types of antibody can be produced against vimentin protein or peptide which is cleaved by caspase-8 between Asp-259 and Val-260: an antibody recognizing the resulting N-terminal fragment (referred to as V1 antibody) and an antibody recognizing the resulting C-terminal fragment (referred to as V2 antibody). See FIG. 1.

When the V1 antibody is produced, a protein or peptide fragment that has the maximum of 259 amino acid residues, preferably 6 amino acid residues, or more preferably 5 amino acid residues, from Asp-259 to the $1^{st}$ Met on the N-terminus among an amino acid sequence shown in SEQ ID NO:3 or 4 can be used as an antigen. Similarly, when the V2 antibody is produced, a protein or peptide fragment that has the maximum of 207 amino acid residues, preferably 6 amino acid residues, more preferably 5 amino acid residues, from Val-260 to Glu-466 on the C-terminus among an amino acid sequence shown in SEQ ID NO: 3 or 4 can be used as an antigen. Further to improve the antigenicity, each of the above protein or peptide fragment is preferably allowed to perform coupling reaction at the terminus other than the one resulted from the cleavage by a caspase. It is preferable for facilitating the coupling reaction that a Cys residue is bound to the protein or peptide terminal.

(2) Production of Monoclonal Antibodies Against Cleavage Product of Vimentin (i) Recovery of Antibody-producing Cells Proteins or peptides as produced in (1) are administered as antigens to mammals, such as a rat, mouse, or rabbit. A dosage of the antigen per animal is 0.1 to 100 mg when no adjuvant is used, and 1 to 100 $\mu$g when an adjuvant is used. The adjuvants include Freund's complete adjuvant (FCA), Freund's incomplete adjuvant (FIA), and aluminum hydroxide adjuvant. Immunization is principally carried out by intravenous, subcutaneous, or intraperitoneal injection. In addition intervals of immunization are not particularly limited. Immunization is carried out for 1 to 10 times, preferably 2 to 5 times, at intervals of from several days to several weeks, preferably 2 to 5 week-intervals. One to 60 days, preferably 1 to 14 days after the final immunization, antibody-producing cells are recovered. Examples of antibody-producing cells include spleen cells, lymph node cells, peripheral blood cells, preferably spleen cells or local lymph node cells.

(ii) Cell Fusion

The antibody-producing cells are allowed to fuse with myeloma cells so as to obtain hybridomas. Myeloma cells to be fused with the antibody-producing cells may include generally available established cell lines of animals, such as a mouse. Preferable established cell lines used herein have drug selectivity and cannot survive in HAT selection medium containing hypoxanthine, aminopterin, and thymidine when unfused, but can survive therein only when fused with the antibody-producing cells. Specific examples of myeloma cells include mouse myeloma cell lines, such as X63Ag.8.653, NSI/1-Ag4-1, and NS0/1; and rat myeloma cell lines, such as YB 2/0.

Next, the myeloma cells are fused with the antibody-producing cells. Briefly, $1\times10^6$ to $1\times10^7$ cells/ml of antibody-producing cells are mixed with $2\times10^5$ to $2\times10^6$ cells/ml of myeloma cells in an animal cell culture medium such as serum-free DMEM or RPMI-1640. Preferable cell ratio of the antibody-producing cells to myeloma cells is 2:1 to 3:1. Then, fusion reaction is performed in the presence of a cell fusion promoter. The cell fusion promotor is, for example polyethylene glycol of an average molecular weight 1,000 to 6,000 daltons. Further, a commercially available cell fusion device using electric pulse stimulation, e.g., electroporation can be used to fuse antibody-producing cells with myeloma cells.

(iii) Selection and Cloning of the Hybridomas

Hybridomas of interest are selected from the fused cells. First, cell suspension is appropriately diluted with such as RPMI-1640 medium containing fetal calf serum, about $3\times10^5$ cells/well are placed in microtiter plate wells, selection medium is added to each wells, and the cells are cultured while appropriately replacing selection medium. Cells growing around 14 days after the start of cultures in selection medium can be obtained as hybridomas.

Next, supernatants from hybridoma cell cultures are examined by screening for the presence of antibody reacting with cleavage product of vimentin. Screening of hybridomas may be performed by any of the conventional methods and not particularly limited. For example, a part of the culture supernatant contained in a well in which a hybridoma has grown may be collected and subjected to screening using an enzyme immunoassay, radioimmunoassay or the like.

Cloning of fused cells is performed by the limiting dilution method or the like. Finally, hybridomas which are cells producing monoclonal antibodies that react with cleavage product of vimentin but not with intact vimentin are established.

(iv) Recovery of Monoclonal Antibodies

Monoclonal antibodies can be recovered from established hybridomas using conventional methods, such as a cell culture method, and ascites formation method.

In the cell culture method, hybridomas are grown in culture media for animal cells, such as 10% fetal calf serum-containing RPMI-1640 or MEM medium, or serum-free medium under conventional culture conditions (for example, at 37° C., under 5% $CO_2$) for 7 to 14 days. Then antibodies are recovered from the culture supernatants.

In the ascites formation method, about $1\times10^7$ cells of hybridomas are administered intraperitoneally to animals belonging to the same species of the mammals from which myeloma cells are derived so that a large number of hybridomas are grown. After 1 to 2 weeks, ascitic fluid is collected.

When purification of antibodies is required in the above described recovery methods, antibodies can be purified by known methods such as an ammonium sulfate method, ion exchange chromatography, gel filtration, and affinity chromatography. These methods may be used independently or in combination.

(3) Production of Polyclonal Antibodies Against the Cleavage Product of Vimentin Antigens prepared as described above are administered to mammals, such as a rat, mouse, and rabbit. A dosage of antigens per animal is 0.1 to 100 mg when no adjuvant is used, and 10 to 1,000 μg when adjuvant is used. The adjuvants used in this invention include Freund's complete adjuvant (FCA), Freund's incomplete adjuvant (FIA), and aluminum hydroxide adjuvant. Immunization is principally carried out by intravenous, subcutaneous, or intraperitoneal injection. Intervals of immunization are not particularly limited. Immunization is carried out for 1 to 10 times, preferably 2 to 5 times, at intervals of from a few days to a few weeks, preferably 2 to 5 week-intervals. Six to 60 days after the final immunization, antibody titer is measured using ELISA (enzyme-linked immunosorbent assay), EIA (enzyme immunoassay) or RIA (radioimmuno assay). On a day that the maximum antibody titer is shown, blood is collected to obtain anti-serum.

Subsequently, reactivity of polyclonal antibodies in antiserum against the cleavage product of vimentin is measured by ELISA, etc. Polyclonal antibodies showing strong reactivity against the cleavage product of vimentin but showing no reactivity against intact vimentin are selected.

For example, polyclonal antibodies in anti-serum are applied to an affinity column to which the cleavage product of vimentin is fixed, thereby recovering antibodies (column adsorption fraction) reacting with the cleavage product of vimentin. Then the resulting antibodies are applied to an affinity column fixed with intact vimentin, thereby recovering antibodies that do not adsorb but flow out are recovered. Finally obtained antibodies are subjected to ELISA to confirm whether they react with the cleavage product of vimentin but do not react with intact vimentin.

2. Method for Detecting Apoptosis

The above antibody may be used to detect (e.g., quantify) the cleavage product of vimentin in the present invention. For example, a sample containing the cleavage product of vimentin may be incubated with the monoclonal antibody or polyclonal antibody of the present invention, followed by an anti-mouse IgG antibody labeled with an enzyme such as horseradish peroxidase (HRP). The amount of the cleavage product of vimentin in the sample may be determined by measuring the intensity of color developed during the enzymatic reaction using a measuring device. The measured value can be used as an indicator for detecting the activity of caspase. A greater value measured represents an increased activity of caspase, indicating that apoptosis of the test cell has progressed.

The antibody of the present invention may also be used to detect apoptosis by reacting the antibody with cells in a biological sample. For example, the sample to be assayed may be incubated with the above antibody. The cleavage product of vimentin present in the sample may be detected and quantified by using an anti-mouse IgG antibody labeled with horseradish peroxidase (HRP) etc. according to conventional methods.

A measured value greater than negative control indicates a higher activity of caspase. On the contrary, a measured value less than positive control indicates a lower activity of caspase. These measured values can be used as data for determining the progression of apoptosis. For example, they may be used as indicators of the progression of autoimmune diseases such as systemic lupus erythematosus (SLE), autoimmune hemolytic anemia and Basedow's disease or acquired immunodeficiency syndrome (AIDS).

3. Reagent Containing the Antibody of the Present Invention

The antibody against the cleavage product of vimentin may be used as various reagents in the present invention. For example, when the antibody is used as a reagent for detecting the cleavage product of vimentin, the detection may be carried out using the procedure shown in Section 2 above. The reagent according to the present invention may include, for example, an anti-mouse IgG antibody labeled with HRP, an anti-rabbit IgG antibody labeled with HRP, a substrate for HRP and a buffer, as well as the above antibody.

Alternatively, when the antibody of the present invention is used as a reagent for immunohistochemical staining, the detection may be carried out according to a conventional procedure for immunohistochemical staining. In this case, the reagent according to the present invention may include, for example, an anti-mouse IgG antibody labeled with HRP, a fluorescently labeled anti-mouse IgG antibody, a substrate for HRP and a buffer, as well as the above antibody. For example, various tissue microscopic sections obtained by biopsy of SLE patient may be prepared by conventional methods to react with the antibody of the present invention. These sections may be incubated with an anti-mouse IgG antibody labeled with horseradish peroxidase (HRP) as a secondary antibody and then treated with a substrate 3,3'-diaminobenzidine to develop brown. The brown area found in the section indicates that caspase has become active in this area.

EXAMPLES

The present invention is further described in the following examples. These examples are provided for illustrative purposes only, and are not intended to limit the scope of the invention.

Example 1

Preparation of Antibodies (a) Materials

Peptides used for immunization were obtained from Biologica Co. (Nagoya, Japan). Activated hemocyanin (Imject Maleimide-KLH) was obtained from Pierce (Rockford, Ill., USA). FMP-activated cellulofine was obtained from Seikagaku Corp. (Tokyo, Japan). Other biochemical reagents were obtained from Sigma-Aldrich Japan (Tokyo, Japan).

(b) Coupling of Chemically Synthesized Peptides to Carrier Proteins

Synthesized peptides (2 mg) were dissolved in Dulbecco's phosphate buffer (hereinafter referred to as PBS; Harlow E. & Lane, D. (1988) "Antibody" Cold Spring Harbor Laboratory Press, Cold Spring Harbor, N.Y., USA). These peptides have the following sequences, respectively: Cys-Gln-Ile-Asp-Val-Asp (SEQ ID NO: 1; referred to as sequence V1) and Val-Ser-Lys-Pro-Asp-Cys (SEQ ID NO: 2; referred to as sequence V2).

Sequences V1 and V2 correspond to five amino acid residues that are immediately N- and C-terminal to the cleavage site by caspase-8 in vimentin protein, respectively and each having Cys residue for coupling reaction at the terminus other than the cleavage site by caspase-8 (FIG. 1). Sequences V1 and V2 were dissolved in 400 μl and 200 μl PBS, respectively. Each solution was mixed with 200 μl of activated hemocyanin (Imject Maleimide-KLH) to start coupling reaction. Each reaction mixture was rotated gently at room temperature for 2.5 hours. The reaction product was dialyzed against PBS at 4° C. to remove unreacted peptides. The resulting peptide-carrier conjugate was diluted with PBS to a final volume of 5 ml.

(c) Immunization

The above peptide-carrier conjugate was mixed well with Freund's adjuvant (Harlow E. & Lane, D. (1988) "Antibody" Cold Spring Harbor Laboratory Press, Cold Spring Harbor, N.Y., USA) and subcutaneously injected into a New Zealand white rabbit for immunization. The peptide-carrier conjugate containing 400 pg of the peptide was used per injection. The rabbit was immunized for 4 times at days 1, 9, 22 and 31. The circulating blood was collected after 8 days of the final immunization to prepare antiserum by conventional methods.

(d) Preparation of Affinity Column for Purifying Specific Antibodies 0.3 g of an activated resin (FMP-activated cellulofine) were swelled in distilled water (50 ml) and filled into Econo-Column (Bio-Rad, Hercules, Calif., USA). The resin in the column was further washed with 10 ml distilled water. One milligram of the synthesized peptide (sequence V1 or V2) was dissolved in 10 ml coupling buffer (50 mM $Na_2CO_3/NaHCO_3$, pH 8.5) and mixed with the resin in the column to start coupling reaction. The coupling reaction continued overnight at 4° C. with rotation. The resin was further incubated with 20 ml blocking buffer (50 mM Tris-HCL, pH 8.0, 0.1 M monoethanolarine) at room temperature for 4 hours with rotation in order to block unreacted resin. Subsequently, unreacted peptides were removed by washing sequentially with the following solutions (20 ml each): 1) distilled water; 2) 0.1M Gly-HCl (pH 2.5); 3) distilled water; 4) washing buffer (20 mM Tris-HCl, pH 7.5, 1 M NaCl, 1% Triton X-100) and 5) distilled water.

The affinity column prepared was washed with 10 ml elution buffer (0.1 M Gly-HCl, pH 2.5), 10 ml distilled water, followed by 20 ml TBS (20 mM Tris-HCl, pH 7.5, 0.15 M NaCl) immediately before used for affinity purification.

(e) Affinity Purification of Specific Antibodies from Antisera

The antiserum (3 ml for sequence V1, 6 ml for sequence V2) was loaded on the above column and mixed well with affinity resin therein. The column was allowed to stand at room temperature for 1 hour to cause binding the antibodies to the resin. To remove non-specifically bound proteins, the column was washed sequentially with the following solutions: 1) 10 ml TBS; 2) 30 ml washing buffer (supra); 3) 30 ml TBS and 4)10 ml of 0.15 M NaCl. The specific antibodies were eluted with 4 ml elution buffer (supra). The protein fraction eluted from the column was mixed immediately with 1 M Tris (0.2 ml) on ice to recover its pH to a neutral range.

Finally, 4 ml of anti-V1 antibody (2.75 mg/ml) and anti-V2 antibody (0.15 mg/ml) were obtained, respectively. These purified antibodies were divided into aliquots and stored frozen at −20° C.

Example 2

Western Blot Analysis Using Specific Antibodies

Human T cell line Jurkat or SKW6.4 ($4 \times 10^5$ cells/ml) was induced to undergo apoptosis by treatment with 200 ng/ml anti-Fas antibody (Medical & Biological Laboratories Co., Ltd., Nagoya, Japan). The treatment continued for 0 to 8 hours at the longest duration. The cells ($2 \times 10^6$ each) were collected by centrifugation (1,000 rpm/min, 5 min) and then suspended in PBS. The cells were centrifuged again under the same condition as defined above to remove culture medium in the sample. Each cell sample was ultrasonically treated for 20 seconds in 40 µl sample buffer (62.5 mM Tris-HCl, pH 6.8, 6 M Urea, 2% sodium dodecylsulfate (SDS), 10% glycerol, 0.003% bromophenol blue) for SDS-polyacrylamide gel electrophoresis. Proteins in each cell lysate sample were separated on 12% polyacrylamide gel electrophoresis (Laemmli, U.K. (1970) Nature, 227, 680–685) and transferred onto a nitrocellulose membrane using Semidry Blot transfer device (Nihon EIDO, Tokyo, Japan) to form Western blots.

The Western blots were immunostained by enzyme chemiluminescence labelling method (ECL) (Harlow E. & Lane, D. (1988) "Antibody" Cold Spring Harbor Laboratory Press, Cold Spring Harbor, N.Y., USA). A primary antibody was a commercially available anti-vimentin antibody V9 (8.8 µg/ml, Sigma-Aldrich Japan, Tokyo, Japan) or the anti-V1 or V2 antibody (0.2 µg/ml). A secondary antibody was an anti-mouse or rabbit IgG antibody labeled with horseradish peroxidase (1000-fold dilution, Cappel, Durham, N.C., USA). Following incubation with the secondary antibody, the Western blots were visualized using ECL Plus kit (Amersham Japan, Tokyo, Japan). Immunostaining was carried out according to the manufacturer's instruction. The results are shown in FIGS. 2 and 3.

Figure 2:
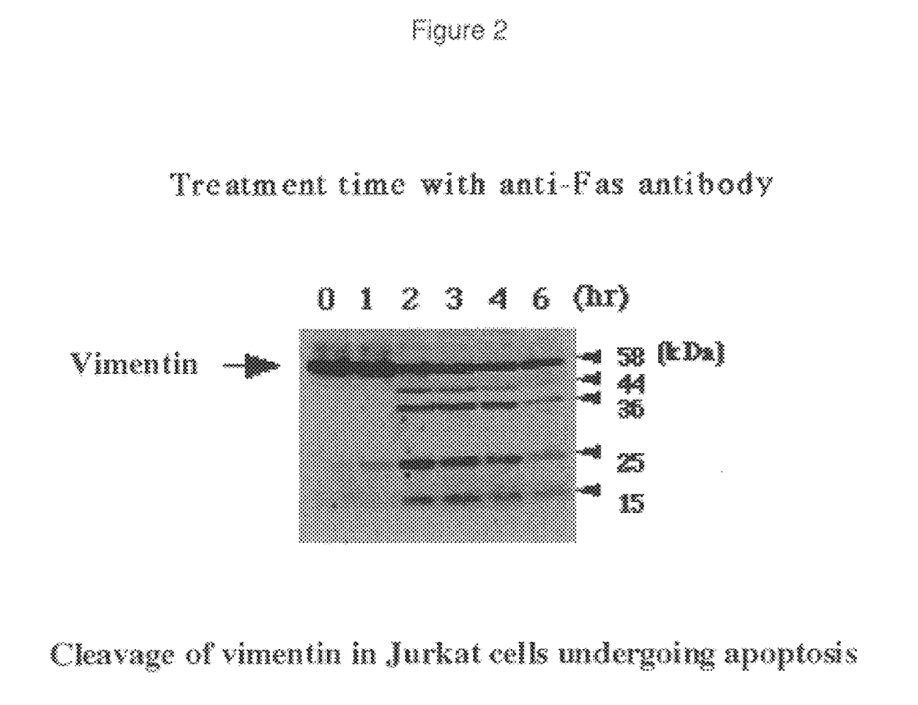
FIGS. 2 and 3 show photographs of Western blot analysis.

FIG. 2 shows Western blots of Jurkat cell lysate treated with the anti-Fas antibody. Following electrophoresis, the blots were immunostained with the anti-vimentin antibody (V9). Upon treatment with the anti-Fas antibody for several hours, caspases cleaved vimentin (58 kDa) at the maximum of three sites into fragments of different size.

Figure 3:
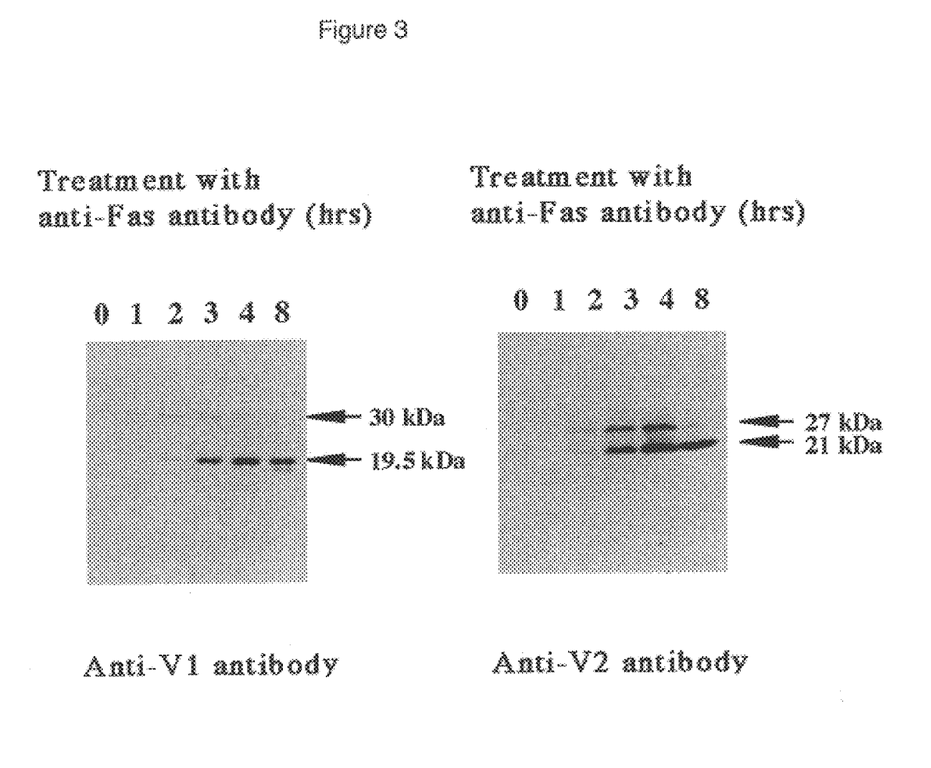

When the lysate of cells undergoing apoptosis was subjected to Western blot analysis using the anti-V1 or V2 antibody, these antibodies specifically stained only vimentin fragments generated by cleavage of the sequence Ile-Asp-Val-Asp (FIG. 3). The anti-V1 antibody detected 30 kDa and 19.5 kDa fragments, while the anti-V2 antibody detected 27 kDa and 21 kDa fragments because other caspases caused further fragmentation almost simultaneously with or subsequently to the fragmentation by caspase-8. On the other hand, neither the anti-V1 nor V2 antibody reacted with intact vimentin (58 kDa) that did not undergo cleavage (see FIG. 3, Lane of hour 0). Hence, FIG. 3 shows that the antibody of the present invention recognizes only vimentin fragments found in cells undergoing apoptosis.

Example 3

Indirect Immunofluorescence Staining of Apoptotic Cells with Specific Antibodies Human T cell line Jurkat ($4 \times 10^5$ cells/ml) was induced to undergo apoptosis by treatment with 200 ng/ml anti-Fas antibody (Medical & Biological Laboratories Co., Ltd., Nagoya, Japan). Following the treatment for 6 hours, the cells ($1.5 \times 10^6$) were collected by centrifugation (1,000 rpm/min, 5 min) and then suspended in PBS. The cells were centrifuged again under the same condition as defined above to remove culture medium in the sample.

The collected cells were fixed in cold methanol at −20° C. for 2 min. The fixed cells were washed with PBS and subjected to indirect immunofluorescence staining (Harlow E. & Lane, D. (1988) "Antibody" Cold Spring Harbor Laboratory Press, Cold Spring Harbor, N.Y., USA). First, the cells were incubated with the anti-V1 or V2 antibody (0.2 µg/ml, in PBS containing 3% bovine serum albumin) at room temperature for 1 hour and washed with PBS to remove unbound antibodies. Next, a fluorescently labeled anti-rabbit IgG antibody (Alexa 448, Molecular Probes, Eugene, Oreg., USA) was used as a secondary antibody, which was diluted 500-fold and added to the above cells for incubation at room temperature for 30 min. The cells were washed with PBS to remove unbound secondary antibodies. PBS had contained a DNA-staining reagent DAPI (0.1 µg/ml, Sigma-Aldrich) in order to visualize nuclear chromosomes. The cells were then examined by Fluorescence Microscope IX70 (Olympus Optical Co., Ltd., Tokyo, Japan).

Figure 4:
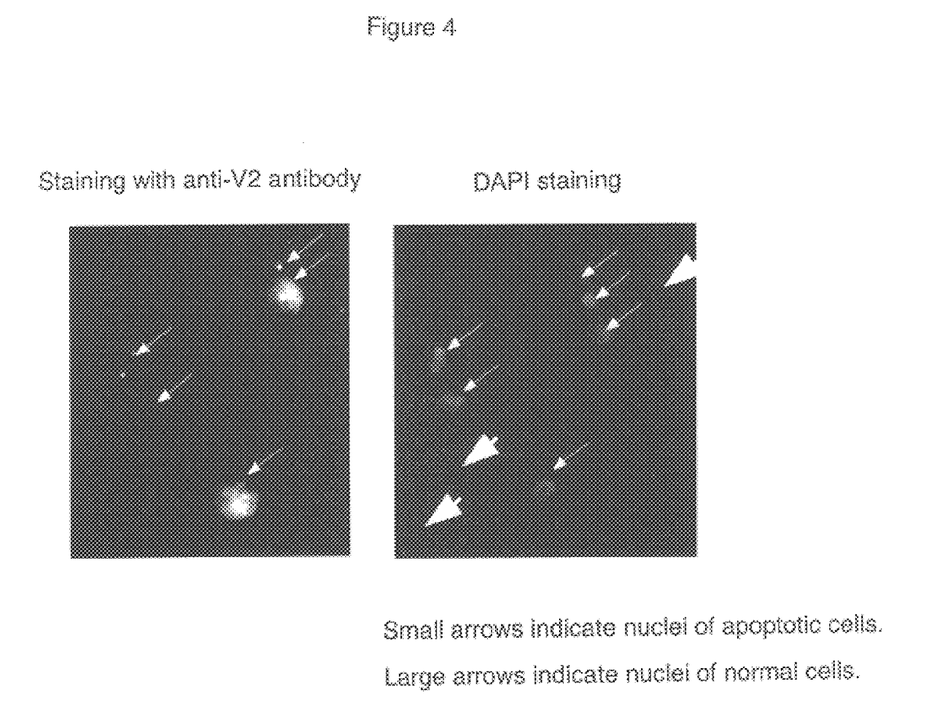
FIG. 4 shows photographs of indirect immunofluorescence staining of apoptotic cells.

The results are shown in FIG. 4. FIG. 4 shows a photograph of the cells are fluorescently stained with the anti-V2 antibody. The apoptotic cells could be identified by condensation and fragmentation of their nucleus when visualized using DAPI (see small arrows in FIG. 4). The anti-V2 antibody was found to specifically stain only cells undergoing apoptosis. Cells that do not undergo apoptosis (see large arrows in FIG. 4) are not stained with the anti-V2 antibody. As a control, Jurkat cells untreated with the anti-Fas antibody were similarly examined, indicating that none of these cells were stained with the anti-V2 antibody.

The antibody of the present invention was shown to react only with the cleavage product of vimentin, but not with intact vimentin.

The present invention can achieve the detection of the actual cleavage of substrates by caspase regardless of sample scale such as protein, cell or tissue. Hence, the present invention enables one 1) to observe the conversion of caspase-8 from its precursor into its active form; 2) to find the active form of caspase-8 to actually function in place within the cell; and 3) to selectively distinguish the cells in which caspase-8 has become active in cell populations.

The present invention provides the antibody that react with the cleavage product of vimentin, but not with intact vimentin. By using the antibody of the present invention, the initiator caspase that is in active form and is cleaving proteins can be identified by detecting the cleavage product of vimentin.

Vimentin is highly expressed in various developing tissues. Also, increased expression of vimentin is often observed when the tissue becomes cancerous. Accordingly, the antibody of the present invention can be a useful reagent for examining caspase activity in developing tissues or cancer cells, for detecting apoptosis, or for deciding therapeutic regimens for apoptosis-related disease.

Free text of Sequence Listing
  SEQ ID NO.: 1: Synthetic peptide
  SEQ ID NO.: 2: Synthetic peptide All publications, patents and patent applications cited herein are incorporated by reference in their entirety.

What is claimed is:

1. A purified antibody that binds specifically to an antigen polypeptide consisting of an N-terminal side or a C-terminal side fragment of vimentin but does not bind to intact vimentin, wherein said N-terminal side fragment comprises about 5 to 6 amino acid residues from the 85$^{th}$, 259$^{th}$, or 429$^{th}$ amino acid residue to Met-1 on the N-terminus in an amino acid sequence shown in SEQ ID NO: 3 or SEQ ID NO: 4, and wherein said C-terminal side fragment comprises about 5 to 6 amino acid residues from the 86$^{th}$, 260$^{th}$, or 430$^{th}$ amino acid residue to Glu-466 on the C-terminus in an amino acid sequence shown in SEQ ID NO: 3 or SEQ ID NO: 4.

2. The antibody of claim 1 wherein said antibody is a polyclonal antibody or a monoclonal antibody.

3. The antibody of claim 1, wherein said N-terminal side fragment consists of the amino acid sequence shown in SFQ ID NO:1.

4. The antibody of claim 1, wherein said C-terminal side fragment consists of the aminio acid sequence shown in SEQ ID NO:2.

5. The antibody of claim 1, wherein said antigen polypeptide consists essentially of an amino acid sequence of SEQ ID NO:1 or SEQ ID NO:2.

6. A purified monoclonal antibody that binds specifically to a cleavage product of vimentin, but that does not bind to intact vimentin, that is produced by the process of:

(a) eliciting an immune response in a vertebrate host by immunizing said host with an antigen polypeptide consisting of an N-terminal side or C-terminal side fragment of vimentin, wherein said N-terminal side fragment comprises about 5 to 6 amino acid residues from the 85$^{th}$, 259$^{th}$, or 429$^{th}$ amino acid residue to Met-1 on the N-terminus in an amino acid sequence shown in SEQ ID NO: 3 or SEQ ID NO: 4, and wherein said C-terminal side fragment comprises about 5 to 6 amino acid residues from the 86$^{th}$, 260$^{th}$, or 430$^{th}$ amino acid residue to Glu-466 on the C-terminus in an amino acid sequence shown in SEQ ID NO: 3 or SEQ ID NO: 4;

(b) preparing a hybridoma from lymphoid cells of said host;

(c) selecting a hybridoma which produces a monoclonal antibody reacting with a cleavage product of vimentin but not reacting with intact vimentin; and (d) obtaining said antibody.

7. The antibody of claim 6, wherein said N-terminal side consists of the amino acid sequence shown in SEQ ID NO:1.

8. The antibody of claim 6, wherein said C-terminal side fragment consists of the amino acid sequence shown in SEQ ID NO:2.

9. The antibody of claim 6, wherein said antigen polypeptide consists essentially of an amino acid sequence of SEQ ID NO:1 or SEQ ID NO:2.

* * * * *

SEQUENCE LISTING

<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 1

Cys Gln Ile Asp Val Asp
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 2

Val Ser Lys Pro Asp Cys
 1               5

<210> SEQ ID NO 3
<211> LENGTH: 466
<212> TYPE: PRT
<213> ORGANISM: Homo sapiens

<400> SEQUENCE: 3

Met Ser Thr Arg Ser Val Ser Ser Ser Tyr Arg Arg Met Phe Gly
 1               5                  10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
        50                  55                  60

```
Ser Ser Ala Val Arg Leu Arg Ser Ser Val Pro Gly Val Arg Leu Leu
 65                  70                  75                  80

Gln Asp Ser Val Asp Phe Ser Leu Ala Asp Ala Ile Asn Thr Glu Phe
                 85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Phe Leu Ile Lys Thr Val Glu
        435                 440                 445

Thr Arg Asp Gly Gln Val Ile Asn Glu Thr Ser Gln His His Asp Asp
450                 455                 460

Leu Glu
465
```

```
<210> SEQ ID NO 4
<211> LENGTH: 466
<212> TYPE: PRT
<213> ORGANISM: Mus sp.

<400> SEQUENCE: 4

Met Ser Thr Arg Ser Val Ser Ser Tyr Arg Arg Met Phe Gly
 1               5                  10                  15

Gly Ser Gly Thr Ser Ser Arg Pro Ser Ser Asn Arg Ser Tyr Val Thr
                 20                  25                  30

Thr Ser Thr Arg Thr Tyr Ser Leu Gly Ser Ala Leu Arg Pro Ser Thr
             35                  40                  45

Ser Arg Ser Leu Tyr Ser Ser Pro Gly Gly Ala Tyr Val Thr Arg
 50                  55                  60

Ser Ser Ala Val Arg Leu Arg Ser Ser Val Pro Gly Val Arg Leu Leu
 65                  70                  75                  80

Gln Asp Ser Val Asp Phe Ser Leu Ala Asp Ala Ile Asn Thr Glu Phe
                 85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Ser Thr Leu Gln Ser Phe Arg Gln
    195                 200                 205

Asp Val Asp Asn Ala Ser Leu Ala Arg Leu Asp Leu Glu Arg Lys Val
210                 215                 220

Glu Ser Leu Gln Glu Glu Ile Ala Phe Leu Lys Lys Leu His Asp Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
    275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Asn Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Leu Glu Ala Ala Asn Tyr Gln Asp Thr Ile Gly Arg Leu Gln Asp Glu
    355                 360                 365

Ile Gln Asn Met Lys Glu Glu Met Ala Arg His Leu Arg Glu Tyr Gln
370                 375                 380
```

```
-continued

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Thr Phe Ser Ser Leu Asn Leu Arg Glu Thr Asn Leu Glu Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465
```